(12) United States Patent
Lee

(10) Patent No.: US 12,137,940 B2
(45) Date of Patent: Nov. 12, 2024

(54) SUCTION DEVICE FOR FOREIGN SUBSTANCES FROM BODY

(71) Applicant: Guk Hyun Lee, Incheon (KR)

(72) Inventor: Guk Hyun Lee, Incheon (KR)

( * ) Notice: Subject to any disclaimer, the term of this patent is extended or adjusted under 35 U.S.C. 154(b) by 0 days.

(21) Appl. No.: 18/011,105

(22) PCT Filed: Apr. 9, 2021

(86) PCT No.: PCT/KR2021/004480
§ 371 (c)(1),
(2) Date: Dec. 16, 2022

(87) PCT Pub. No.: WO2021/256676
PCT Pub. Date: Dec. 23, 2021

(65) Prior Publication Data
US 2023/0172637 A1 Jun. 8, 2023

(30) Foreign Application Priority Data
Jun. 19, 2020 (KR) ........................ 10-2020-0074816

(51) Int. Cl.
*A61B 17/50* (2006.01)
(52) U.S. Cl.
CPC ................................ *A61B 17/50* (2013.01)
(58) Field of Classification Search
CPC ... A61B 17/24; A61B 17/50; A61B 2017/306; A61B 2017/00752
See application file for complete search history.

(56) References Cited

U.S. PATENT DOCUMENTS

| 2,267,636 A | * | 12/1941 | Benton | ................... | A61B 17/50 |
| | | | | | 604/315 |
| 2012/0221010 A1 | * | 8/2012 | DeLuca | ................. | A61B 17/24 |
| | | | | | 606/106 |

FOREIGN PATENT DOCUMENTS

| KR | 20000002301 U | 2/2000 |
| KR | 20130005162 U | 8/2013 |
| KR | 20150122490 A | 11/2015 |
| KR | 20200000289 U | 2/2020 |
| WO | 2020113123 A1 | 6/2020 |

* cited by examiner

*Primary Examiner* — Anh T Dang
(74) *Attorney, Agent, or Firm* — Maschoff Brennan

(57) ABSTRACT

The present invention relates to a suction device for foreign substances from the body, which may comprise: a suction body that has an internal space, extends a predetermined length, and is brought into contact with the skin; a gripping tube body that extends from the suction body so as to be able to slide up and down along the outer circumferential surface of the suction body, and which can be wrapped and gripped by hand; and a piston body that is connected to the gripping tube body to be provided in the internal space of the suction body and selectively generates a negative pressure in the internal space while interlocking with the up-and-down motion of the gripping tube body. According to the present invention, foreign substances that penetrated the skin can be quickly sucked and removed through a simple operation.

3 Claims, 10 Drawing Sheets

[FIG. 1]
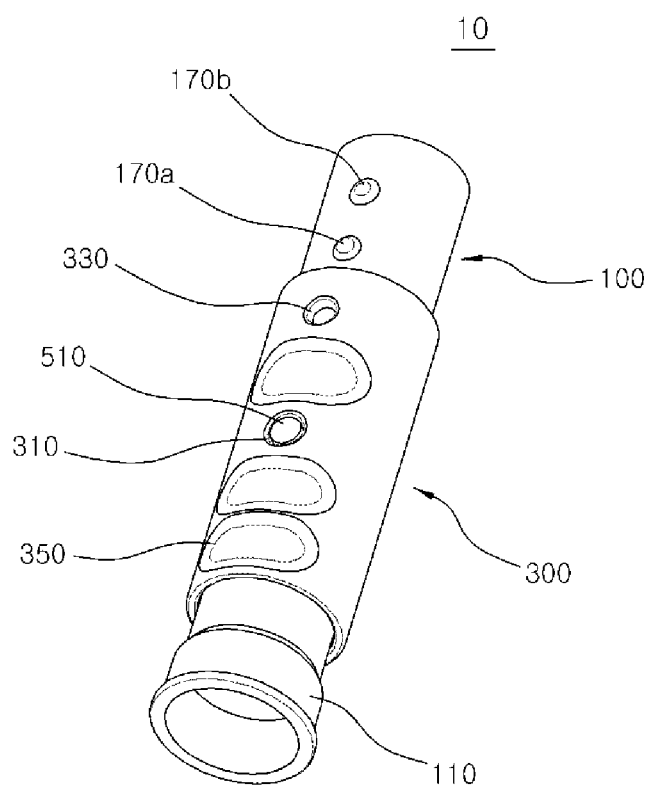

[FIG. 2]
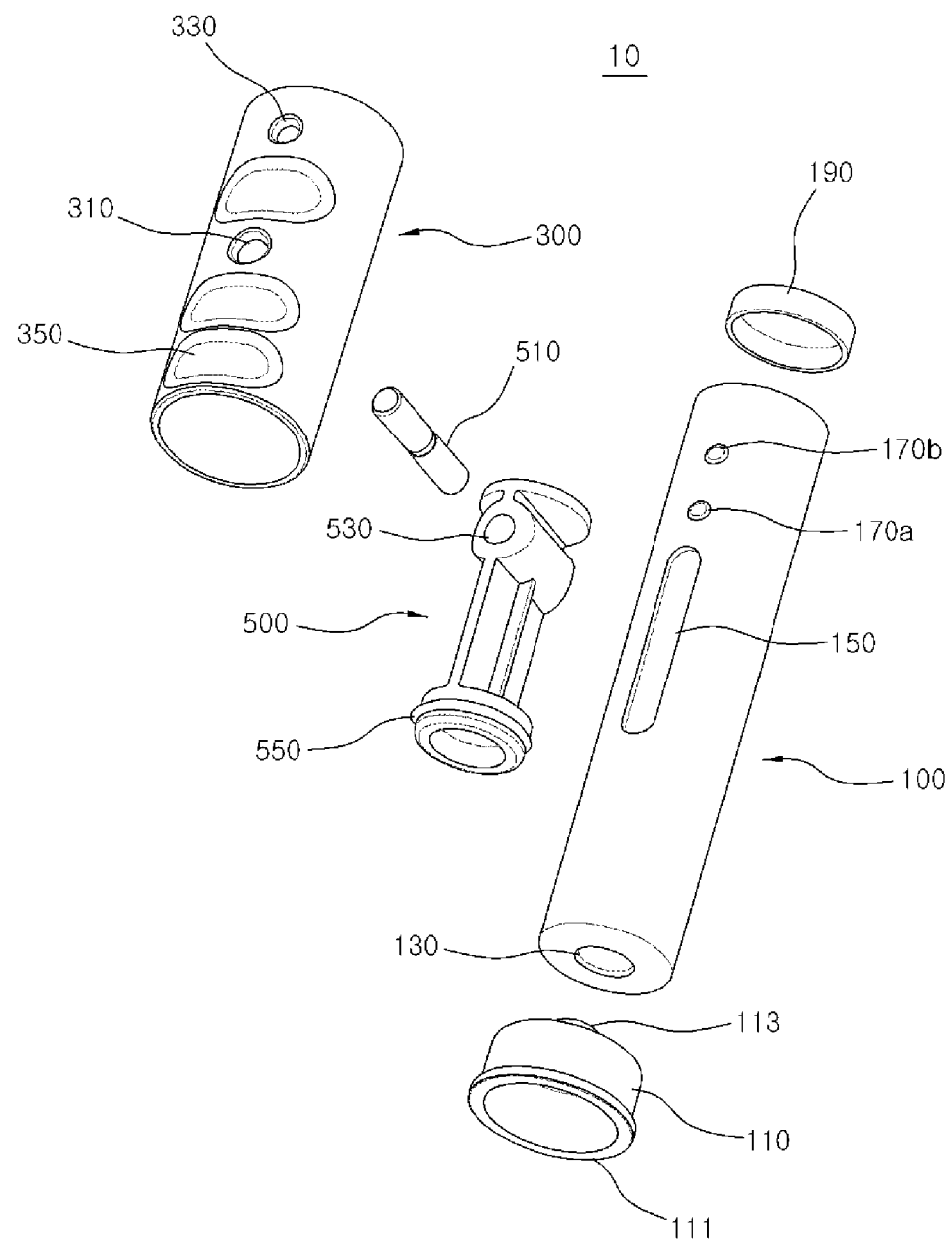

[FIG. 3]
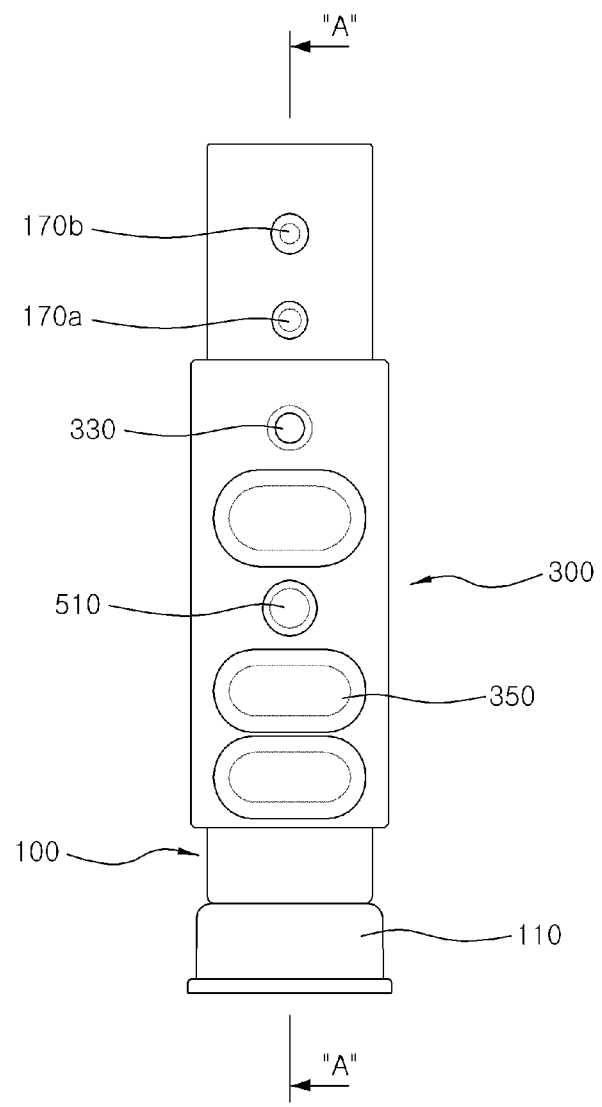

[FIG. 4]
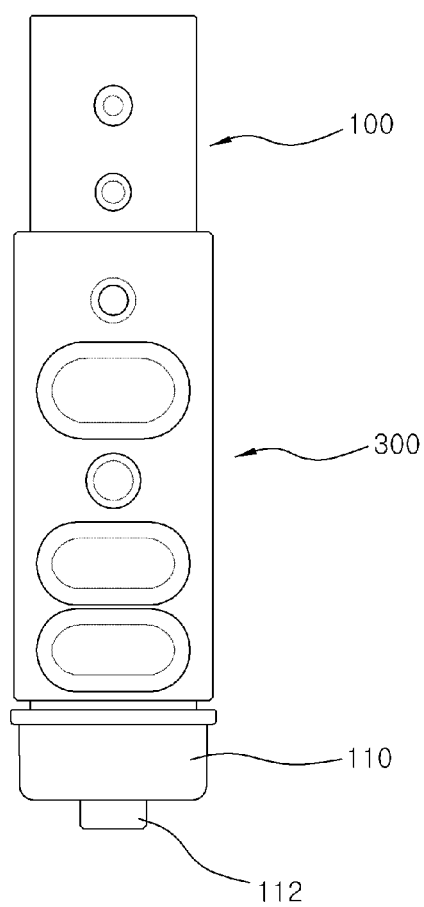

[FIG. 5]
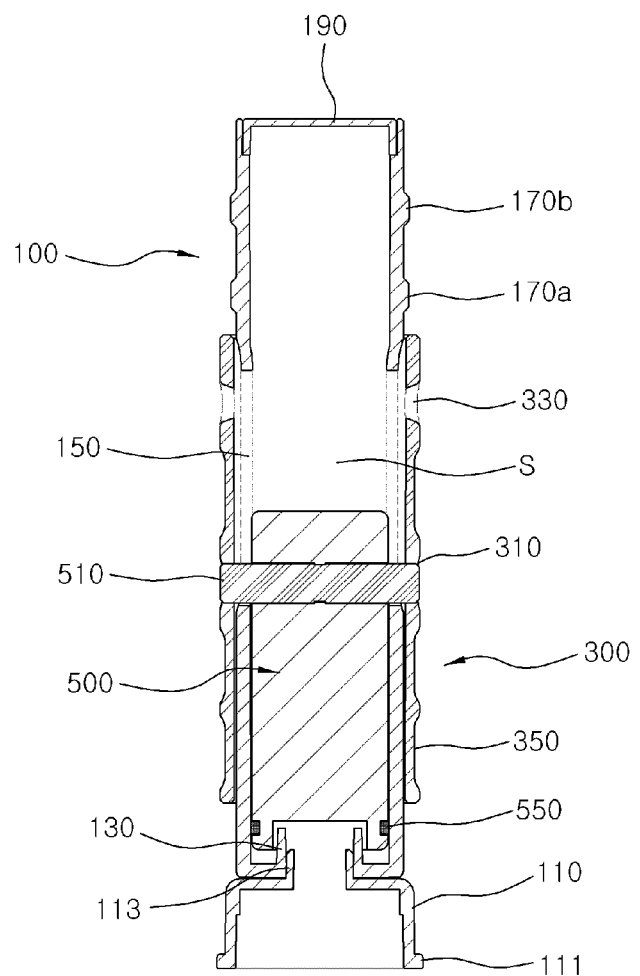

[FIG. 6]
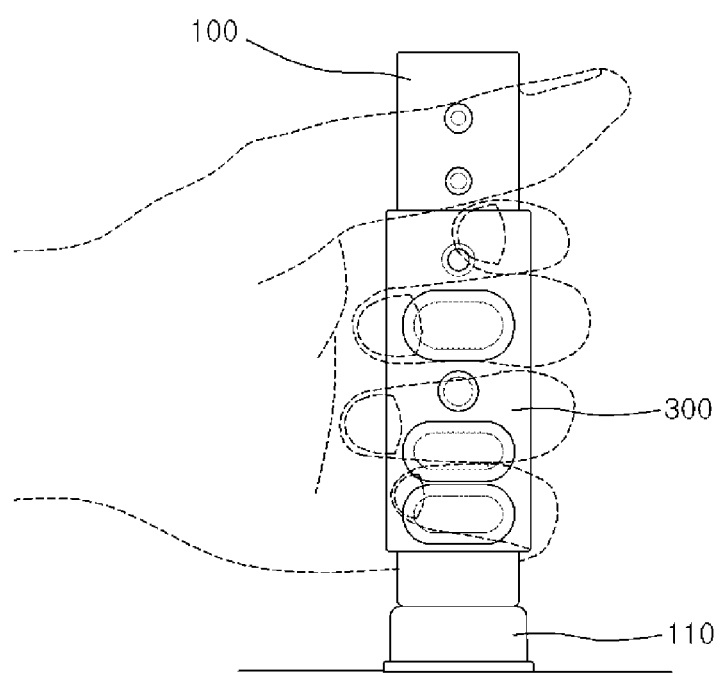

[FIG. 7]
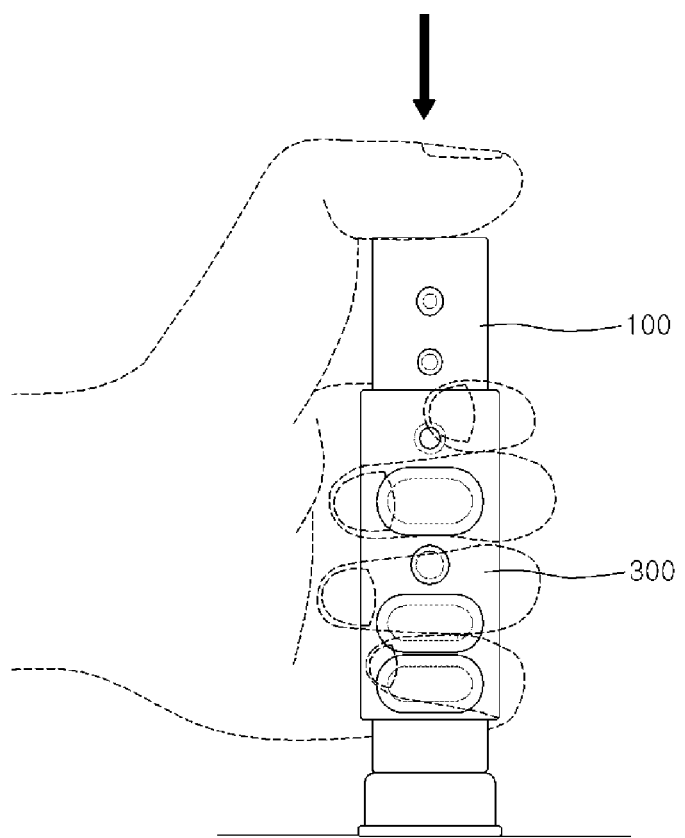

[FIG. 8]
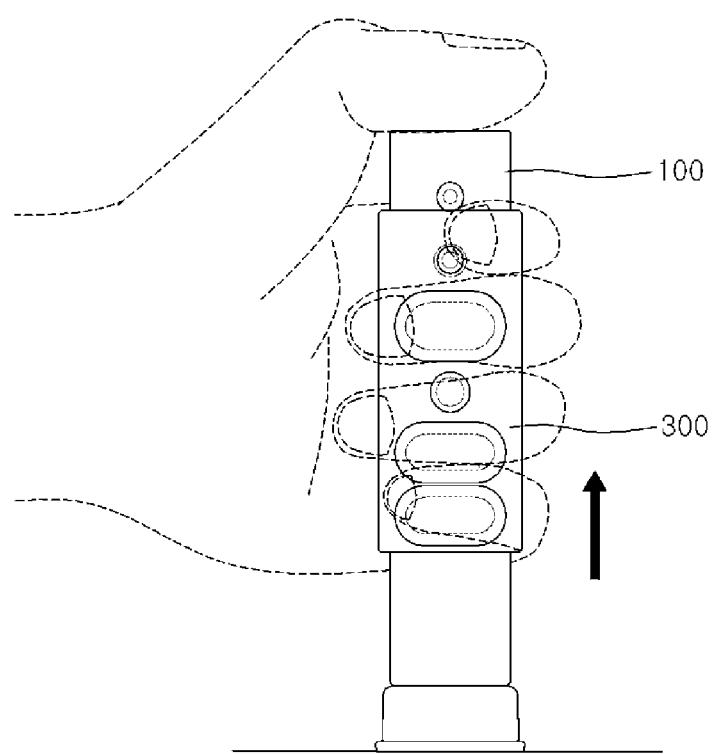

[FIG. 9]
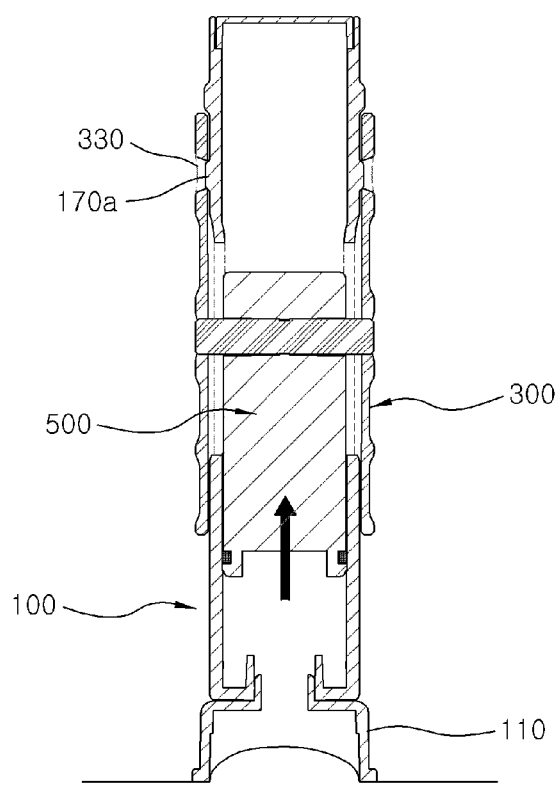

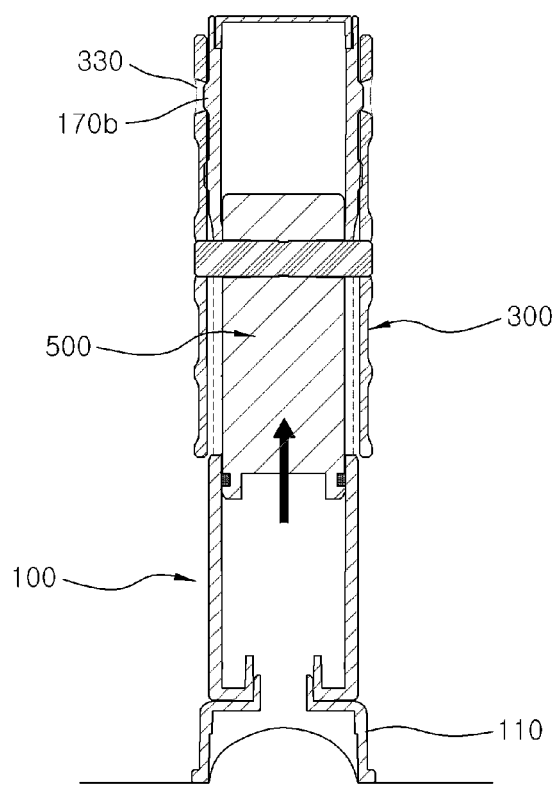
[FIG. 10]

SUCTION DEVICE FOR FOREIGN SUBSTANCES FROM BODY

FIELD OF INVENTION

The present invention relates to a foreign substance inhaler capable of quickly inhaling and removing foreign substances penetrated into the skin by a simple operation when bitten by pests.

BACKGROUND OF INVENTION

As the population who enjoys climbing, camping and leisure activities continues to increase, accidents of bug bites or stings by insects such as mosquitoes, ants, bees, etc., poisonous insects, snakes, or the like, occur frequently. In this case, it is desirable to remove stings, saliva or poison of the insects as soon as possible.

Further, even if not going outdoors, mosquitoes inhabiting apartments and the like appear regardless of the season, causing a lot of harms to people, and some people even visit a hospital due to an allergic response.

Accordingly, in order to solve the above problems, various devices have been proposed to quickly remove foreign substances such as stings, saliva, liquid, poison, etc. of the pest that have penetrated into the skin when bitten or stung by the pest.

Among them, a representative example is a foreign substance inhaler that inhales foreign substances penetrated into the skin by attaching a cylindrical body to the skin site bitten by an insect, putting two fingers in handles on both sides of the body and pulling the body to create a negative pressure inside the body.

However, since the conventionally disclosed foreign substance inhaler has a structure in which a handle is put by two fingers and then pulled upward from the body, it could not be operated with only one hand, or even if being operated, entails much inconvenience and difficulty.

In addition, there are many parts in the body where it is difficult to pull the handle due to angle of the hand, such as the back neck, shoulder, hip, etc., therefore, there are lots of restrictions on the body parts that are useable by a user alone. Further, since the handle must be pulled and held while inhaling foreign substances, it is troublesome and difficult to use the above inhaler.

SUMMARY OF INVENTION

Technical Problem to be Solved

An object of the present invention is to provide a foreign substance inhaler that can be easily and conveniently operated with only one hand in an operation manner to press the inhaler while gripping (or holding) the same, with regard to suction and removal of foreign substances such as saliva, poison, etc. of pest having penetrated into the skin, and that can be used more widely without limitation to body parts.

Technical Solution

In order to achieve the above object,
there is provided a foreign substance inhaler, including: a suction body that has an inner space, extends a predetermined length, and comes into contact with the skin; a gripping tube that is extrapolated to the suction body so as to slide up and down along an outer circumferential surface of the suction body, and is wrapped and held by the hand; and a piston body that is connected to the gripper tube, embedded in the inner space of the suction body, and selectively generates a negative pressure in the inner space while interlocking with up-and-down motion of the gripping tube.

Effect of Invention

According to the foreign substance inhaler of the present invention,
when a user presses the suction body with the thumb of one hand while gripping the gripping tube with the hand, suction operation is performed so that it has an advantage of efficiently suctioning and removing foreign substances in the skin by operating the inhaler easily and comfortably with only one hand.

Further, according to the gripping and pressing structure, suction operation is possible regardless of the angle of the hand, thereby having an advantage that even the user alone can widely use the inhaler in different body parts without particular restrictions.

In addition, since the operation state may be fixed, there is no need to continuously hold and press the gripping tube during inhalation while a suction force is adjustable according to the situation, therefore, it is very convenient to use.

BRIEF DESCRIPTION OF DRAWINGS

FIG. 1 illustrates a foreign substance inhaler according to an embodiment of the present invention.

FIG. 2 illustrates an exploded configuration of the foreign substance inhaler according to an embodiment of the present invention.

FIG. 3 is a front view of the foreign substance inhaler according to an embodiment of the present invention.

FIG. 4 illustrates a cross-sectional configuration of the foreign substance inhaler taken along line "A-A" of FIG. 3.

FIG. 5 illustrates a state in which a contact head is fitted to the suction body.

FIG. 6 illustrates an example of using the contact head in close contact with the skin in a state of holding the gripping tube.

FIG. 7 illustrates a use example of pressing the suction body with the thumb in a state of holding the gripping tube.

FIG. 8 illustrates a use example in which the gripping tube is relatively raised (or goes upward) to the suction body.

FIGS. 9 and 10 illustrate a use example in which a negative pressure is generated in the suction body by first and second lifting of a piston, respectively, thereby applying the suction force to the same.

DETAILED DESCRIPTION OF PREFERRED EMBODIMENTS OF INVENTION

Hereinafter, preferred embodiments of the present invention will be described in detail with reference to the accompanying drawings.

The shape, size, number, spacing between elements, etc. of the elements in the accompanying drawings may be reduced or exaggerated to emphasize a clearer description, and are not limited to those illustrated in the drawings.

Further, terms indicating directions such as front, back (rear), left, right, top, bottom, etc. are only used to describe the directions shown and observed in the drawings. Therefore, it should be understood that, if the directions shown and observed are changed, these terms may also vary.

One embodiment of the present invention is illustrated in FIGS. 1 to 5.

As exemplified in FIGS. 1 and 2, the foreign substance inhaler 10 (hereinafter, abbreviated as "inhaler") according to an embodiment of the present invention may comprise a suction body 100, a gripping tube 300 and a piston body 500.

First, the suction body 100 is a body portion of the inhaler 10 of the present invention, in which suction of foreign substances in the skin may be performed while the suction body is in direct contact with the skin.

The suction body 100 may have a cylindrical shape extending a predetermined length while having an inner space S.

The length of the suction body 100 may be formed to be relatively longer than a length of the gripping tube 300, such that the gripping tube 300 to be described later may move up and down along an outer circumferential surface in an extrapolated state.

Further, the suction body 200 may be formed with a length sufficient to support and press an upper end with the thumb of open hand in a state in which the user wraps and grips the gripping tube 300 with the above hand when the extrapolated gripping tube 300 is in a lowered state.

The suction body 100 may be provided with a contact head 110 that is detachably coupled to a lower end of the suction body 100 and is in direct contact with the skin.

The contact head 110 may have a contact frame 111 in close contact with the skin, which is formed at a bottom end of the contact head, while having a fitting hole 113 protruding from the center of a top end of the contact head.

A through-hole 130 extending inward by a predetermined length may be formed in the center of the lower end of the suction body 100 to corresponding to the fitting hole 113.

Therefore, as the fitting hole 113 is fitted to the through-hole 130, the contact head 110 may be detachably coupled to the lower end of the suction body 100 while communicating with the inner space S.

In this regard, the contact head 110 may be formed to be transparent so that the user can visually check the internal skin condition or an inhalation process of penetrant materials while being in close contact with the skin.

Further, the contact head 110 may have an inner circumferential surface corresponding to the outer circumferential surface of the suction body 100. Therefore, as illustrated in FIG. 5, when not in use, the contact head 110 may be extrapolated to the outer circumferential surface at the lower end of the suction body 100 in an inverted state, so as to be more conveniently carried and stored.

On the other hand, a lateral side of the suction body 100 is cut by a predetermined length in a vertical direction to thus have a long guide hole 150 penetrating the inside and outside of the suction body 100.

The long guide hole 150 may be formed in a pair of left and right holes on both sides of the suction body 100, and such long guide holes 150 may enable lifting and lowering (up-and-down motion) without interference of a connector pin 510 to be described later.

Further, on the lateral side of the suction body 100, a stop protrusion may be formed protruding from an upper portion of the long guide hole 150.

The stop protrusion may be inserted into a protrusion hole 330 of the gripping tube 300 to be described later and may function to secure the relatively vertical position of the gripping tube 300 with respect to the suction body 100.

Such stop protrusion may be formed in plurality while being spaced apart from one another at regular intervals up and down. For example, as illustrated in the drawing, a pair of first stop protrusion 170a and second stop protrusion 170b spaced up and down at a regular interval may be formed.

The first stop protrusion 170a is firstly inserted into the protrusion hole 330 when the gripping tube 300 rises relative to the suction body 100, while the second stop protrusion 170b may be secondly inserted into the protrusion hole 330 when the gripper tube further rises.

The first stop protrusion 170a and the second stop protrusion 170b may be formed in left and right pairs on both sides of the suction body 100, respectively.

Further, the upper end of the suction body 100 is closed wherein the upper end may be integrally connected to a lateral side of the suction body so as to be closed, however, as illustrated in the drawings, a separate closing cap 190 may also be coupled and closed while opening the upper end.

The suction body 100 with the above configuration may be in close contact with the skin through the contact head 110, and the upper end may be pressed by the thumb of the hand holding the gripping tube 300, which will be described later, whereby relative up-and-down motion of the gripping tube 300 occurs and a negative pressure is created in the inner space S by a piston body 500 interlocking with the gripping tube 300, which will be described later, to thus apply a suction force to the skin in close contact with the suction body and inhale foreign substances penetrated into the skin.

Next, the gripping tube 300 is a part to be held by the user's hand that manipulates the piston body 500 when the penetrant material is inhaled.

The gripping tube 300 may be in a circular tube shape having both open upper and lower ends, and may be extrapolated to and installed in the suction body 100.

That is, the gripping tube 300 may be inserted and installed outside the suction body 100 so as to surround the outer circumferential surface of the suction body 100.

Further, the gripping tube 300 may move up and down while sliding along the outer circumferential surface of the suction body 100 in an extrapolated state to the suction body 100.

To this end, an inner diameter of the gripping tube 300 may be slightly larger than an outer diameter of the suction body 100 so that a gap enabling sliding is formed between an inner circumferential surface of the gripping tube 300 in a circular tube shape and the outer circumferential surface of the suction body 100 in a cylindrical shape.

Further, the gripping tube 300 may have a relatively shorter length than the suction body 100 so as to be able to slide up and down along the outer circumferential surface of the suction body 100.

Further, since the gripping tube 300 is held by the user's hand, it may have a length sufficient to be wrapped and gripped by the hand. That is, the gripping tube 300 may have a length similar to or slightly shorter than a vertical width of the user's palm.

The gripping tube 300 may be provided with a pin insertion hole 310 in which one end of a connector pin 510 to be described later is fitted and fixed.

The pin insertion hole 410 may be formed at an intermediate position in a longitudinal direction of the gripping tube 300, and may be formed as a pair on both of left and right sides.

Further, the gripping tube 300 may include a protrusion hole 330 into which the first and second stop protrusions 170a and 170b formed on the suction body 100 may be selectively fitted, wherein the protrusion hole 330 may also be formed in pairs on the left and right sides to correspond to the first and second protrusions 170a and 170b.

Further, the gripping tube 300 may be provided with a finger groove 350 recessed at a predetermined depth to be caught on the finger when the user wraps and grips the gripping tube 300 with his or her hand, thereby preventing slippage.

The finger groove 350 may be formed in plural up and down in order to correspond to a plurality of fingers wrapping the gripping tube 300, and the plurality of finger grooves 350 may be formed as a pair on both of the left and right sides, respectively.

Next, the piston body 500 is a part to generate a negative pressure in the inner space S of the suction body 100 so that the foreign substance is inhaled.

The piston body 500 may be accommodated and installed in the inner space S of the suction body 100 to move up and down and, when lifted in a state of being lowered toward the lower end of the suction body 100, may create a negative pressure.

The piston body 500 may be connected to the gripping tube 300 to interlock with the up-and-down motion of the gripping tube 300, and for this purpose, the piston body 500 may include the connector pin 510.

The connector pin 510 is fitted into the piston body 500 at one end while the other end of the connector pin passes through the long guide hole 150 and then is fitted into the pin insertion hole 310 of the gripping tube 300, thereby enabling the piston body 500 and the gripping body 300 to be interconnected.

The connector pin 510 is provided as a pair on both of the left and right sides so that the piston body 500 can be firmly connected with the gripping tube 300.

Further, a pin fixture 530 for coupling with the connector pin 510, to which the connector pin 510 is fitted and fixed, may be formed on an upper portion of the piston body 500.

Further, the piston body 500 may be provided with a packing ring 550 on a lower portion of thereof, in order to accommodate airtightness with the inner circumferential surface of the suction body 100.

Hereinafter, the operation of the present invention will be described with reference to FIGS. 6 to 10.

When bitten by pests such as mosquitoes, as illustrated in FIG. 6, a user may operate the inhaler of the present invention such that the contact head 110 of the suction body 100 is firstly brought into close contact with the skin of the bitted site in a state in which the gripping tube 300 is wrapped and held by one hand.

At this time, the gripping tube 300 and the piston body 500 are in a state of being lowered toward the lower end of the suction body 100 and, if it has been raised, it can be moved down and come into close contact with the skin.

When the suction body 100 is in close contact with the skin through the contact head 110 in this way, after lifting the thumb of the hand holding the gripping tube 300 upward and seating it to the upper end of the suction body 100, as illustrated in FIG. 7, the upper end of the suction body 100 is pressed by putting some strength in the thumb.

When the upper end of the suction body 100 is pressed in this way, if the suction body 100 is in a state of not receiving any support as if located in the air, the suction body 100 is pressed while the gripping tube 300 is held so that the suction body 100 would descend relatively with respect to the gripping tube 300.

However, in the case of the suction body 100, it is in close contact with the skin and supported. Therefore, as illustrated in FIG. 8, when the suction body 100 is pressed, the gripping tube 300 rises relative to the suction body 100 as opposed to the case where it is not supported.

In other words, when a force is applied by pressing the suction body 100 with the thumb while holding the gripping tube 300 by the hand, the pressed suction body 100 is supported by the skin and movement thereof is restricted, so that the gripping tube 300 would rise relatively along the outer circumferential surface of the suction body 100.

Further, the raised gripping tube 300 may be fixed in the lifting position since the first stop protrusion 170a is firstly inserted into the protrusion hole 300.

On the other hand, as illustrated in FIG. 9, the piston body 500 connected through the connector pin 510 also rises inside the suction body 100 while interlocking with the same according to the relative lifting of the gripping tube 100 with respect to the suction body 100 as described above.

In this regard, since the connector pin 510 connecting the gripping tube 300 and the piston body 500 ascends along the long guide hole 150, any interference does not occur.

As the piston body 500 moves upward, a negative pressure is created in the inner space S of the suction body 100 to thus apply a suction force to the skin to which the contact head 110 is in close contact.

Further, owing to the suction force, the contact head 220 may be adsorbed to the skin while pulling the skin inward, thereby performing foreign substance inhalation to extract and suck the foreign substances from the skin.

During such inhalation, the contact head 110 is in a state of being adsorbed to the skin and the lifted gripping tube 300 is secured with a predetermined force by the first stop protrusion 170a, so that application of the suction force and inhalation of the foreign substance may be retained as it is even if the user's hand holding the gripping tube is released.

Meanwhile, if the suction body 100 is pressed by applying more force in the above state, the gripping tube 300 may be further raised and the second stop protrusion 170b may be secondly inserted into the protrusion hole 300, thereby enabling fixation at a further lifting position.

Further, as illustrated in FIG. 10, as the gripping tube 300 is further raised, the piston body 500 may also further rise while interlocking with the same, thereby increasing the negative pressure in the inner space S of the suction body 100 and eventually applying a greater suction force to the skin.

As described above with respect to the present invention in detail, the inhaler of the present invention is operated in such a way that the suction body is pressed with the thumb of one hand while wrapping around the gripping tube by the hand, so that it is easy and convenient to operate with only one hand without any inconvenience. Further, it can be seen that the inhaler is applicable and usable in different body parts without limitation.

Further, since the lifting state of the gripping tube can be fixed step by step, it is not necessary to continuously hold and press the inhaler during inhalation. Further, it can be seen that the suction force is adjustable according to the use condition whereby use convenience is very excellent.

The preferred embodiments of the present invention have been described in detail above, however, the technical scope of the present invention is not limited to the contents in the above-described embodiments and drawings. Accordingly, equivalent configurations modified or altered by those skilled in the art will be interpreted not to depart from the scope of the technical spirit of the present invention.

The invention claimed is:

1. A foreign substance inhaler, consisting of:
   a suction body consisting of a cylindrical member extending a predetermined length while having a cylindrically shaped-inner space having the same cross-sectional area at an upper end and a lower end of the cylindrically shaped-inner shaped space, a long guide hole formed by cutting the cylindrical member to a predetermined length in a vertical direction, and a pair of stop protrusions formed protruding on an outer circumferential surface of the cylindrical member of the suction body at an upper side of the long guide hole while being spaced up and down at a predetermined interval;

a gripping tube that is extrapolated to the cylindrical member of the suction body so as to slide up and down along the outer circumferential surface of the cylindrical member of the suction body; and a piston body that is connected to the gripping tube, embedded in the cylindrically shaped-inner space of the cylindrical member of the suction body to move up and down in the cylindrically shaped-inner space of the cylindrical member of the suction body, and selectively generates a negative pressure in the cylindrically shaped-inner space while interlocking with up-and-down motion of the gripping tube, wherein the cylindrical member of the suction body is formed to be relatively longer than the gripping tube, wherein an upper end of the cylindrical member of the suction body is able to be pressed by the thumb of the hand holding the gripping tube such that when a force is applied by pressing the upper end of the cylindrical member of the suction body with the thumb while holding the gripping tube by the hand, the gripping tube rises relatively along an outer circumferential surface of the suction body and the piston body rises inside the cylindrical member of the suction body according to the relative lifting of the gripping tube with respect to the suction body and thus the negative pressure is created in the cylindrically shaped-inner space of the cylindrical member of the suction body.

2. The inhaler according to claim 1, wherein the piston body is connected to the gripping tube by a connector pin penetrating the long guide hole.

3. The inhaler according to claim 2, wherein a protrusion hole is formed in the gripping tube into which the pair of stop protrusions is selectively inserted.

* * * * *